(12) United States Patent
Gao

(10) Patent No.: US 11,724,053 B2
(45) Date of Patent: Aug. 15, 2023

(54) DEVICE FOR GRIPPING AND SECURING AN INTUBATION BOUGIE

(71) Applicant: Boyi Gao, Fox Point, WI (US)

(72) Inventor: Boyi Gao, Fox Point, WI (US)

( * ) Notice: Subject to any disclaimer, the term of this patent is extended or adjusted under 35 U.S.C. 154(b) by 502 days.

(21) Appl. No.: 16/837,122

(22) Filed: Apr. 1, 2020

(65) Prior Publication Data
US 2021/0308403 A1    Oct. 7, 2021

(51) Int. Cl.
| | | |
|---|---|---|
| A61M 16/04 | (2006.01) | |
| A61B 1/00 | (2006.01) | |
| A61B 1/267 | (2006.01) | |
| A61M 25/01 | (2006.01) | |

(52) U.S. Cl.
CPC ....... *A61M 16/0488* (2013.01); *A61B 1/0014* (2013.01); *A61B 1/00066* (2013.01); *A61B 1/267* (2013.01); *A61M 25/0113* (2013.01)

(58) Field of Classification Search
CPC combination set(s) only.
See application file for complete search history.

(56) References Cited

U.S. PATENT DOCUMENTS

| | | | |
|---|---|---|---|
| 3,802,440 A | 4/1974 | Salem | |
| 4,211,234 A | 7/1980 | Fisher | |
| 4,244,362 A * | 1/1981 | Anderson | ......... A61M 16/0418 |
| | | | 128/207.14 |
| 4,502,482 A | 3/1985 | DeLuccia et al. | |
| 4,699,138 A | 10/1987 | Behrstock | |
| 4,865,586 A | 9/1989 | Hedberg | |
| 4,892,095 A | 1/1990 | Nakhgevany | |
| 5,016,614 A | 5/1991 | MacAllister | |
| 5,058,577 A | 10/1991 | Six | |
| 5,257,620 A | 11/1993 | Schermerhorn | |
| 5,287,848 A | 2/1994 | Cubb | |
| 5,509,408 A * | 4/1996 | Kurtis | ............... A61M 16/0486 |
| | | | 128/207.14 |
| 5,520,175 A | 5/1996 | Fry | |
| 5,595,172 A | 1/1997 | Reese | |
| RE35,595 E | 8/1997 | Six | |
| 5,733,242 A * | 3/1998 | Rayburn | ............... A61B 1/0052 |
| | | | 600/143 |
| 5,842,973 A | 12/1998 | Bullard | |
| 6,146,402 A | 11/2000 | Munoz | |
| 6,443,156 B1 * | 9/2002 | Niklason | ............... A61M 16/04 |
| | | | 128/207.14 |
| 7,243,653 B2 | 7/2007 | Nelson | |
| 8,161,967 B2 | 4/2012 | Hamms et al. | |
| 10,080,854 B1 | 9/2018 | Pifer | |
| 10,272,217 B2 * | 4/2019 | Gao | .................. A61M 16/0488 |
| 10,478,578 B2 * | 11/2019 | Esnouf | .............. A61M 16/0488 |
| 2007/0017527 A1 | 1/2007 | Totz | |
| 2008/0276932 A1 | 11/2008 | Bassoul | |

(Continued)

FOREIGN PATENT DOCUMENTS

| | | |
|---|---|---|
| GB | 2542640 | 3/2017 |
| WO | WO2011/012677 | 2/2011 |

*Primary Examiner* — Monica E Millner
(74) *Attorney, Agent, or Firm* — Ryan Kromholz & Manion, S.C.

(57) ABSTRACT

An apparatus for endotracheal intubation. The apparatus allows medical personnel to grip and stabilize a bougie inside the apparatus and maintain a curved orientation during the intubation processes. The apparatus includes a locking ring for retaining the bougie during use.

18 Claims, 12 Drawing Sheets

(56) References Cited

U.S. PATENT DOCUMENTS

| | | | |
|---|---|---|---|
| 2009/0125002 A1* | 5/2009 | Totz | A61M 16/04 |
| | | | 128/207.15 |
| 2010/0121152 A1 | 5/2010 | Boedeker | |
| 2010/0249513 A1 | 9/2010 | Tydlaska | |
| 2011/0120458 A1* | 5/2011 | Schwartz | A61B 1/267 |
| | | | 128/200.26 |
| 2012/0065471 A1 | 3/2012 | McGrath | |
| 2012/0178996 A1* | 7/2012 | Tydlaska | A61B 1/0676 |
| | | | 600/186 |
| 2014/0107422 A1* | 4/2014 | Huels | A61B 1/00105 |
| | | | 600/188 |
| 2014/0128681 A1* | 5/2014 | Fordinal | A61B 1/267 |
| | | | 600/194 |
| 2014/0166000 A1* | 6/2014 | Olympio | A61M 16/0488 |
| | | | 128/200.26 |
| 2014/0238390 A1 | 8/2014 | Wei | |
| 2015/0034078 A1* | 2/2015 | Sovndal | A61M 16/0488 |
| | | | 128/200.26 |
| 2015/0173598 A1* | 6/2015 | Alexander | A61B 1/015 |
| | | | 600/187 |
| 2016/0038014 A1 | 2/2016 | Molnar | |
| 2017/0224200 A1 | 8/2017 | Uesugi | |
| 2017/0246410 A1 | 8/2017 | Levitan | |
| 2017/0325667 A1 | 11/2017 | Babarro et al. | |
| 2018/0318534 A1 | 11/2018 | Desatnik | |

* cited by examiner

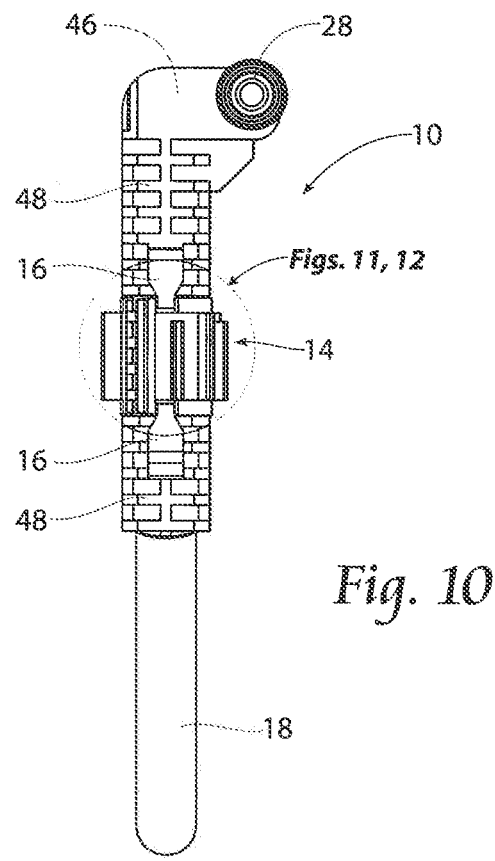
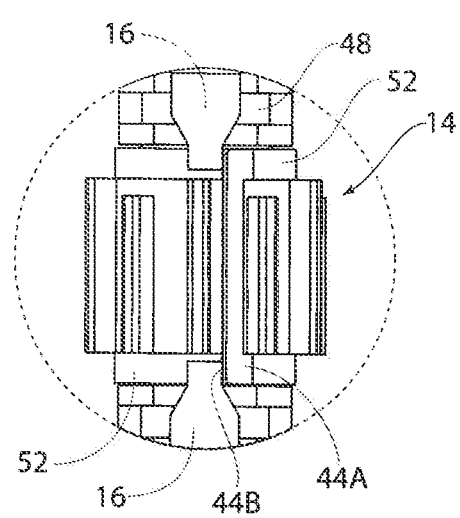
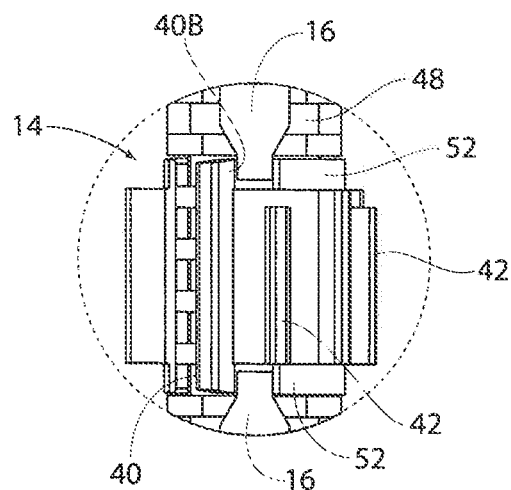
Fig. 10
Fig. 11
Fig. 12

DEVICE FOR GRIPPING AND SECURING AN INTUBATION BOUGIE

BACKGROUND OF THE INVENTION

The present invention relates to a bougie device and method of use thereof, and more particularly relates to a device for gripping and directing a bougie device which is suitable for guiding insertion of an endotracheal tube into an airway of a person.

A bougie may have numerous uses in medicine, but are commonly used to widen a passageway or guide another instrument into a passageway. An intubation aide commonly known as the "gum elastic bougie" is a thin, solid or hollow, cylinder of rubber, plastic or another material that a physician inserts into a body passageway. Within the art of tracheal intubation, bougies are frequently used as a guide for the correct placement of an endotracheal tube. Bougies are also used to provide suction or oxygen delivery within a body passageway.

Bougies generally require a necessary level of flexibility so that they can navigate a body passageway, with the required flexibility resulting in bougies that are hard to grip. Devices have been designed to assist in intubation of the bougie, i.e. guiding the bougie, but such devices still have limitations in allowing for adequate gripping of the bougie so that it can be properly navigated during a procedure.

In many medical situations endotracheal intubation is a critical procedure performed to secure a patient's airway. To facilitate insertion of an endotracheal tube, a physician, paramedic or other medical personnel will use a laryngoscope blade which is inserted down a patient's throat. The laryngoscope blade is primarily used to move the tongue and the epiglottis from the providers view in order to provide a clear passage to the vocal cords. Placement of the endotracheal tube correctly in the patient's trachea must be done quickly to avoid hypoxic brain injury to the patient. The task of endotracheal intubation becomes more challenging in emergent situations, patients with difficult airways and those that are at high risk for aspiration.

Commonly in the operating room prior to induction of general anesthesia patients are given 100% oxygen to breath in effort to replace nitrogen in the lungs with oxygen. This process is known as preoxygenation and serves to fill the lungs with oxygen like a reservoir. When patients undergo general anesthesia they become apneic and must rely on the oxygen reservoir within the lungs to provide oxygen for the bodies basic metabolic needs. Sufficient pre-oxygenation adequately fills the lungs with oxygen to provide more time for the medical personnel to instrument the airway and attempt endotracheal intubation.

Evaluation of a patient's airway allows physicians to gauge the difficulty that may be encountered when attempting endotracheal intubation. Certain clinical features of patient such a large neck circumference, obesity, history of sleep apnea, small mouth opening, and overbite among others are predictors of a difficult endotracheal intubation. Once a patient has been deemed to have a difficult airway, the physician may obtain equipment such as a video laryngoscope or intubation aide like the bougie. A physician may have a poor view of a patient with a difficult airway of the vocal cords under direct laryngoscopy, which would make endotracheal intubation difficult. The bougie is vital tool in the difficult airway as it has a bended tip that facilitates its passage into the patient's trachea.

Commonly found within hospitals is suction tubing with a handle attached, also known as a yankauer, which are used to aspirate fluid within the patient's airway. Under direct laryngoscopy, the yankauer provides direct vision of the patient's vocal cords. In an effort to overcome these problems, medical personnel often insert the yankauer to remove blood, oral secretions, or gastric content prior to proper placement of the endotracheal tube. After aspiration of fluid within the pharynx the suction device must be removed and an endotracheal tube must be inserted within the trachea. This two step procedure of clearing secretions, gastric contents, or blood with the suction tube removing it and then grabbing an endotracheal tube results in lost time. However, these prior art processes use valuable time, along with the patient's oxygen reservoir, switching between devices. Moreover, even when suction tube is inserted into the mouth it is possible fluids to reaccumulate in between the time suction tube is removed and endotracheal tube insertion.

If an intubation attempt fails, then the patient must be ventilated with bag and mask device which can force air down the trachea as well as down the esophagus. When the stomach is extended with air, patient becomes more likely to vomit and aspirate. A distended abdomen also decreases a patient's lung compliance and makes it more difficult to ventilate. Moreover, repeated intubation involves instrumenting the airway with laryngoscope blade which causes trauma to the patient which can result in bleeding and edema. It is vital that endotracheal intubation be accomplished quickly, accurately, atraumatically and on consistently on the first attempt. Repeated attempts with intubation often make endotracheal intubation even more challenging. A distended abdomen from bag-mask ventilation, bleeding, or edema can obstruct the physician's view of the vocal cords and places the patient at risk for aspiration. This is a common problem with the current intubation procedure with a difficult airway has been taking time to exchange between using the bougie, yankauer, and the endotracheal tube. This lost time puts the patient at risk for aspiration pneumonia, aspiration pneumonitis, or hypoxic brain injury.

SUMMARY OF THE INVENTION

The present invention provides a gripping device for a solid or hollow bougie or bougies during an intubation procedure. The gripping device has a curved channel, which allows the gripping device to receive a bougie. Once the bougie is nested within the channel, the device also has a locking device which allows the gripping device to securely maintain the bougie within the channel, while still allowing the bougie to slide within the channel. The extended curved channel with the locking device will hold a bougie more steadily and allow a user to more easily insert a bougie into a patient's trachea.

Preferably, the locking device is in the form of a locking ring.

The present invention also provides methods for intubating a patient, wherein a bougie is inserted into the patient's airway. The insertion is assisted by a gripping device, which securely locks the bougie in place, while allowing the bougie to be adjusted inwardly and outwardly with respect to the airway.

The present invention may further comprise a suction bougie that can be used to aspirate fluids as well as an intubation guide for insertion of an endotracheal tube into the airway of a patient. The hollowed bougie can be connected to external tubing, e.g. suction tubing or oxygen tubing.

Commonly, when medical personnel performs a direct laryngoscopy of a patient's airway for adequate visualization of the vocal cords, the presence of oral sections, blood, masses, or gastric contents is unwanted.

The airway device mentioned above is primarily used for patients with a difficult airway, or who are at risk for aspiration of gastric contents. Management of these patients often necessitates that an intubation guide commonly known in the field as gum elastic "bougie" and an oral suction device. The bougie may be used if there is poor visualization of the vocal cords and a suction apparatus is needed to clear oral secretions or gastric contents to provide an unobstructed view of the vocal cords. The use of either the bougie or suction requires the medical personnel to switch between handling either device. The proposed invention allows the medical personnel to use the bougie and suction simultaneously without having to spend time to exchange devices. This ultimately removes inherent delays in securing the airway.

The invention as mentioned functions as an apparatus that attaches to a bougie to facilitate endotracheal intubation. The apparatus may be attached to a pre-existing bougie intubation aid as well a suction bougie, which is designed as a hollow tube. The suction bougie may comprise an elongated body that is hollow at both the proximal and distal ends. The distal end of the tube may have several open ports to allow for passage of oral secretions, blood, or gastric contents. The proximal end is connected to a suction port.

The body of the bougie device may be formed from Teflon, polytetrafluoroethylene, or plastic polymer, resulting in a self-lubricated device. This reduces the need for the bougie device to be lubricated for insertion into the airway of a patient.

The present invention is designed with a curved handle that has a support channel to receive either a solid or hollow bougie. The handle preferably will generally be rigid and preferably manufactured from a hard plastic material.

The proximal end of the handle encompasses a hollow tube with one end attached to the proximal end of the suction bougie or an oxygen delivery bougie. The handle is designed with a recess where the bougie is meant to reside within with an outside force, i.e. the gripping force of the user's fingers, which also forces the bougie into the curvature of the recess, thus stabilizing the bougie by increasing the gripping area during intubation.

After the bougie is attached to the proximal end of the handle, the bougie is then bent around itself with its distal portion nested within the curved handle. The other end of the hollow tube of proximal handle is connected to suction tubing or oxygen tubing commonly found within hospital and surgical facilities.

The hollow tube may feature a vent port that, when occluded by the medical personnel's finger, will allow suction force from the distal tip of the suction bougie. When the vent port is not occluded, no suction force will be provided at the tip of the suction bougie. A vent port allows medical personnel to have complete control over when to utilize suction. A suction device that lacks such complete control may cause continuous suction of oxygen from the patient oropharynx and subsequent hypoxia. The invention can be used as an oxygen delivery device as well.

The present invention also allows for telescopic advancement of an endotracheal tube over a bougie prior to advancement of a bougie into a patient's trachea. The endotracheal tube can be immediately advanced over the bougie into the trachea.

The apparatus may be used with the pre-existing bougie to provide a more ergonomic way to use the bougie. The bougie is commonly manipulated by the medical personnel to incorporate a curve for endotracheal insertion. The curve of the bougie is meant to follow the natural curvature of the patient's oropharynx. However, a common problem that is encountered with bougie use has been its difficulty navigating a patient's oropharynx. The physical properties of the bougie make it flimsy and bendable which can make it difficult for the medical personnel to control. The apparatus is designed with a curved channel in which the bougie is placed. Once the bougie is nested within the apparatus, a locking ring secures the bougie to the apparatus.

BRIEF DESCRIPTION OF THE DRAWINGS

FIG. 10 is a front view of the gripping device of the present invention;

FIG. 11 is a close up view taken from FIG. 10 of the ring in an open position;

FIG. 12 is a close up view taken from FIG. 10 of the ring in a locked position;

DETAILED DESCRIPTION

As will be seen, the present invention overcomes many problems associated with prior art with intubation of a difficult airway, high risk of aspiration, or emergent endotracheal intubation. Upon induction of general anesthesia, unconscious patients, certain medical conditions render patients at risk for aspiration of gastric contents. Conditions like morbid obesity, diabetic gastroparesis, pregnancy, hiatal hernia, and full stomach increases the risk of aspiration upon induction of general anesthesia. The invention allows the operator to clear oral secretions, gastric contents, and blood from the operator's field of view to safely intubate the patient.

Figure 1A:
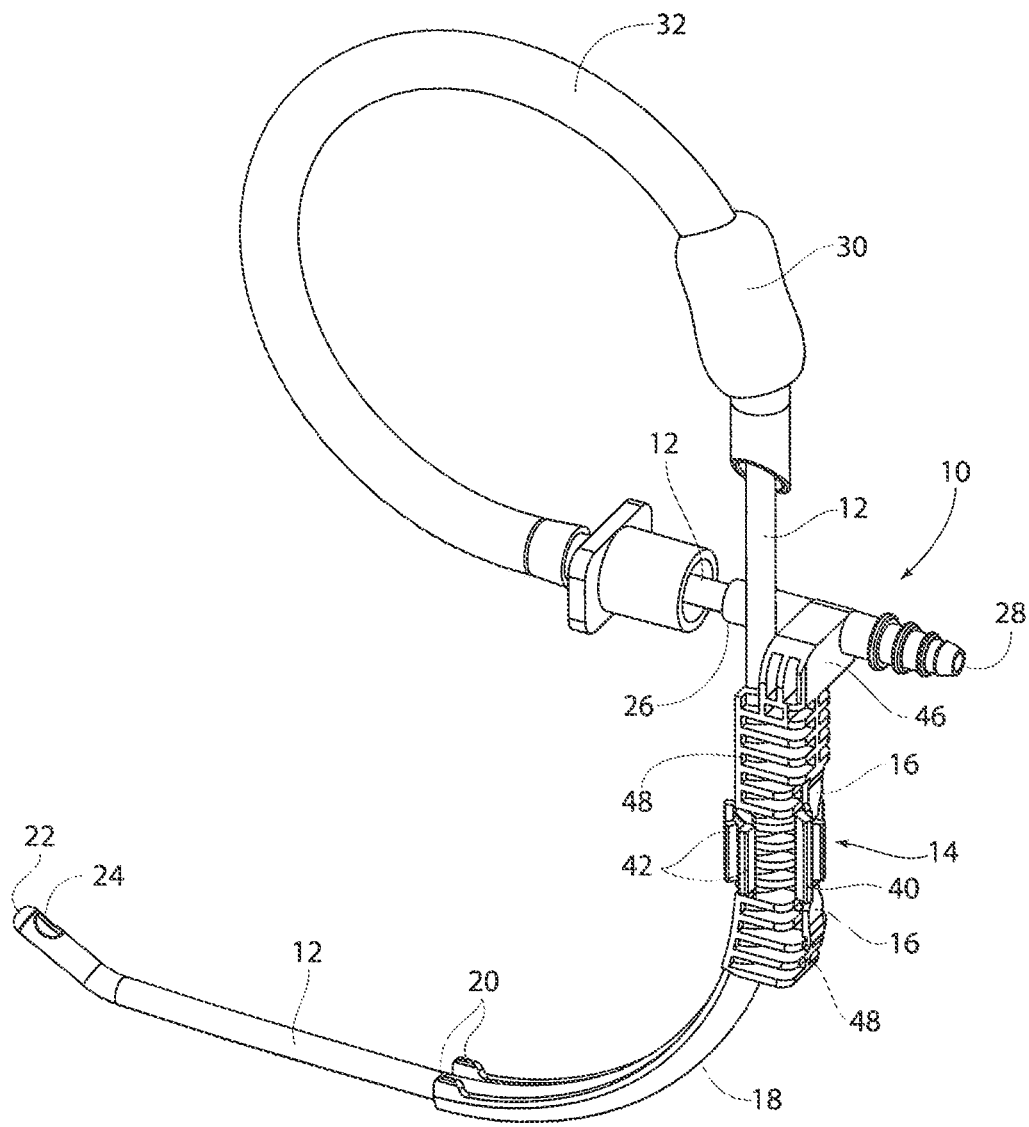
FIG. 1A is a perspective view of a gripping device according to the present invention, including a bougie attached to a handle having a locking ring.
Figure 1B:
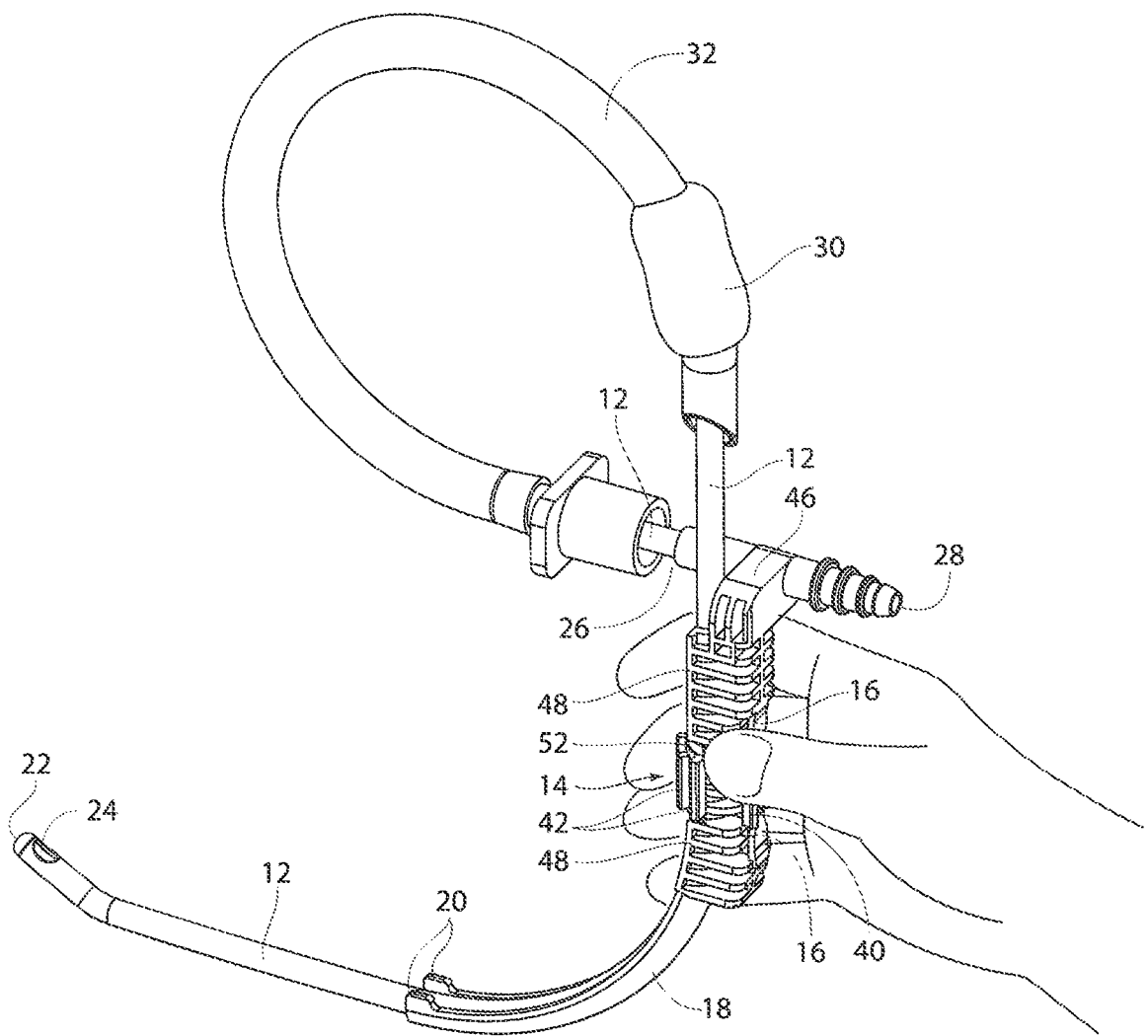
FIG. 1B is the same as FIG. 1, now showing a user gripping the handle.

FIG. 1A depicts a bougie handle 10 according to the present invention, and FIG. 1B depicts handle 10 in use. The handle 10 encloses a bougie 12, and a locking ring 14 is provided to retain bougie 12 within handle 10. As will be discussed in further detail below, the locking ring allows for the bougie 12 to be securely retained and locked in place, while still allowing the bougie to be slid inwardly and outwardly with respect to a patient's airway when intubating a patient. Handle 10 has a top end, a bottom end, and a plurality of gripping ridges, and as shown in FIG. 1B, this permits one handed operation by turning the locking ring either with the thumb or middle finger.

Figure 2:
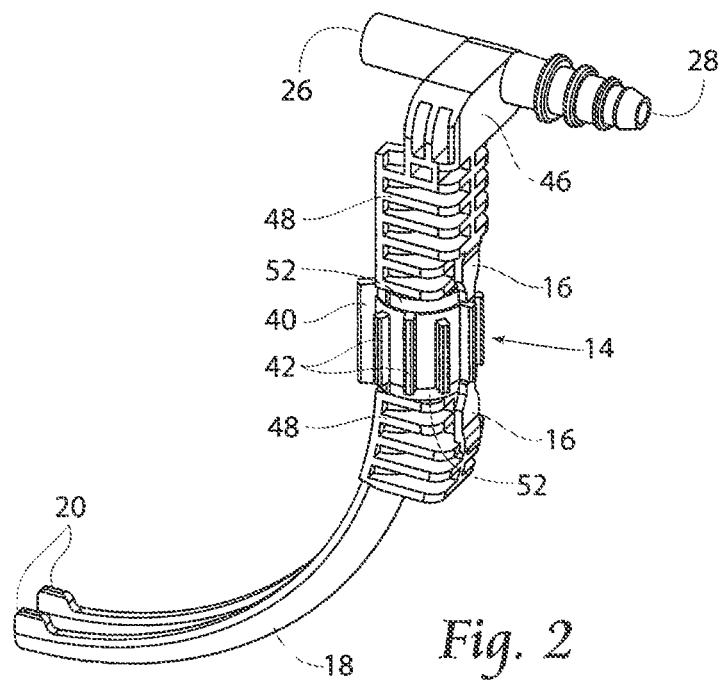
FIG. 2 is a front perspective view of a first embodiment of the gripping device of the present invention.

Referring to FIG. 2, the handle 10 is further provided with flexible stop tabs 16, a bougie support channel 18, and bougie channel retainers 20. Bougie 12 has a proximal end 22 and a proximal opening 24. Bougie 12 also has a distal inlet 26 and outlet 28. FIG. 1 further shows apparatus for intubation, including an intubation balloon 30 and tube 32. FIGS. 1A and 1B also illustrate the presence of an elbow turn segment 46 for connecting handle 10 to inlet/outlet 26/28.

Figure 4:
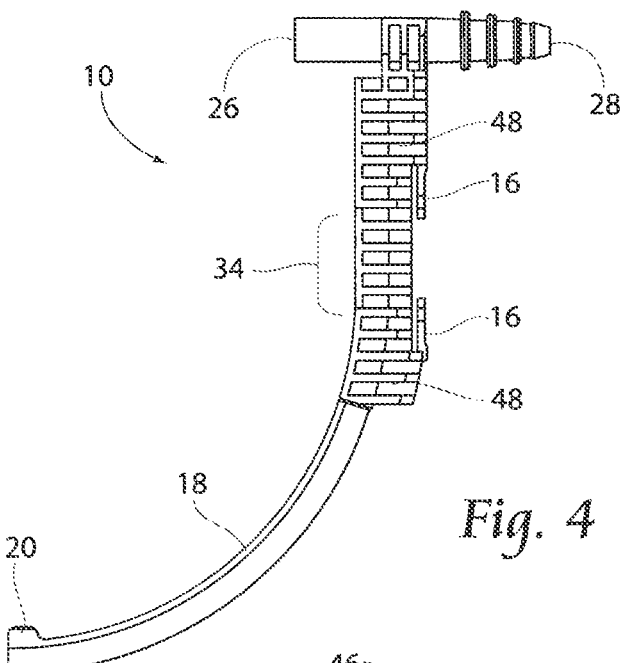
FIG. 4 is a side view of the device shown in FIG. 2, now shown without a locking ring.
Figure 5:
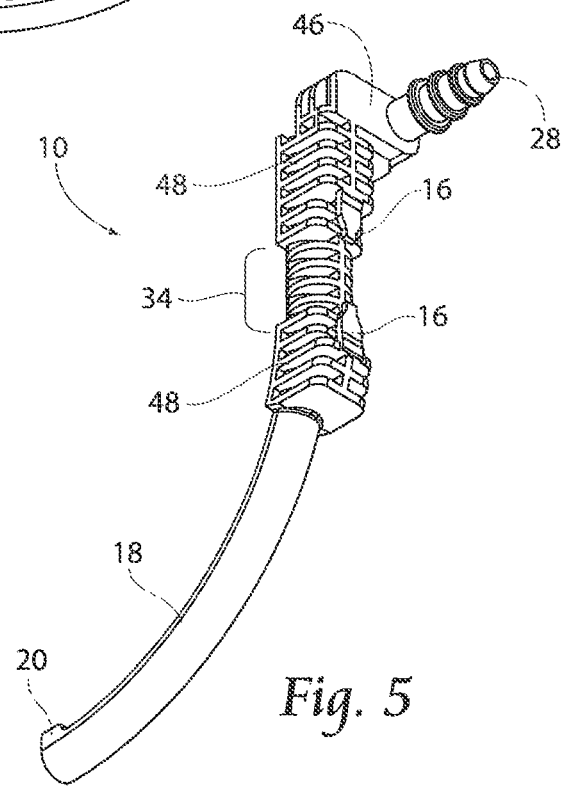
FIG. 5 is a bottom perspective view of FIG. 4.

Turning to FIGS. 4 and 5, handle 10 can be seen without associated locking ring 14, showing that handle 10 has a reduced diameter section 34 for retaining and permitting rotation of locking ring 14. Flexible tabs 16 can be clearly seen in these figures. Referring to FIGS. 4 and 5, handle 10 is shown without associated locking ring 14.

Locking ring 14 is shown from several views in FIGS. 6-9, and illustrate its possible features. These include an opening 36 and an inner surface 38 made to permit ring 14 to snap onto reduced diameter section 34 and rotate thereon in sliding engagement.

At least a first, leading finger member 40 and a plurality of additional finger members 42 are spaced apart around the circumference of ring 14. As can be seen in FIG. 1B, these allow the user to manipulate ring 14 about section 34 with finger/thumb pressure.

Figure 6:
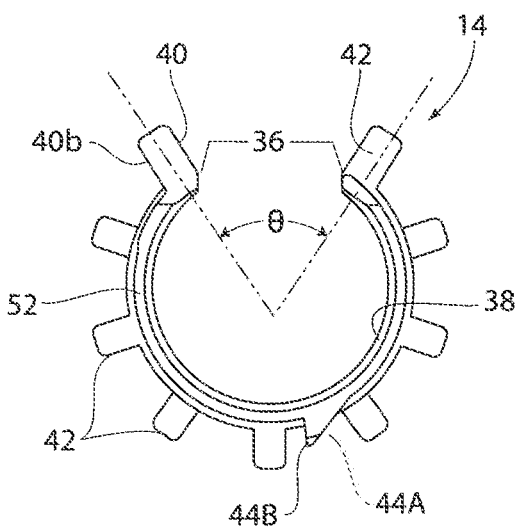
FIG. 6 is an end view of a locking ring of the present invention showing angle θ.

FIG. 6 is an end view of ring 14 showing angle θ being created by the intersection of lines extending from leading member 40 and the member 42 adjacent opening 36. The angle may be of any effective angle to permit ring 14 to snap onto and be retained by section 34. Opening 36 is sized to be complementary to the diameter of surface 38 for the same purpose.

Figure 7:
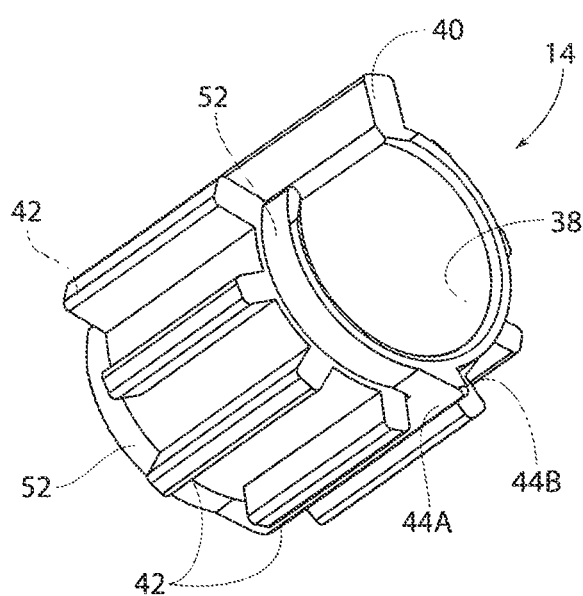
FIG. 7 is a side perspective view of FIG. 6.

Locking ring 14 features extension collars 52 at each end, as seen for example in FIG. 7. Enlarged ring end 40 is coextensive with collars 52 while fingers 42 do not extend as far as collars 52. Collars 52 are located and held underneath tabs 16 and also held by being shaped to fit the reduced diameter section 34.

Figure 8:
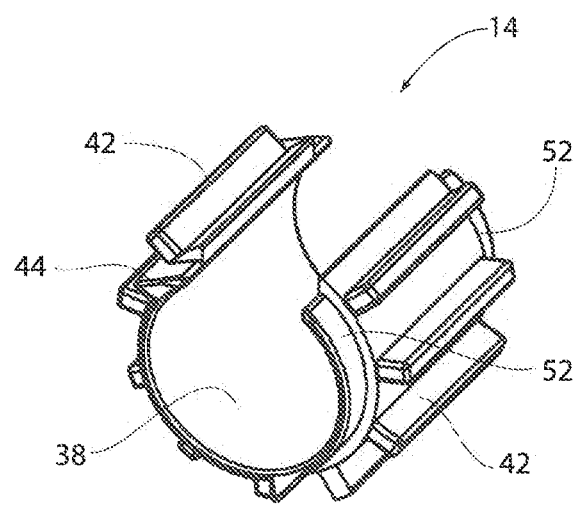
FIG. 8 is a view of another embodiment of the ring of the present invention.
Figure 9:
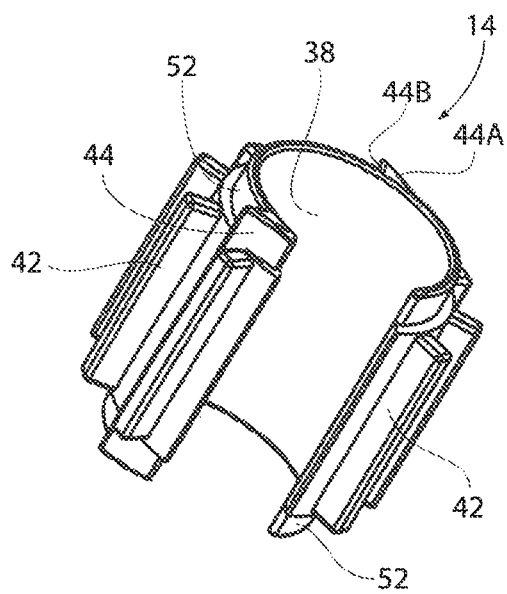
FIG. 9 is another view of the embodiment shown in FIG. 8.

FIGS. 6-8 also illustrate the existence of at least one stop rib 44 having a slope side 44A and a stop side 44B. As seen in FIG. 9, two stop ribs 44 may be provided. Additional stop ribs 44 may be provided as desired.

Figure 22:
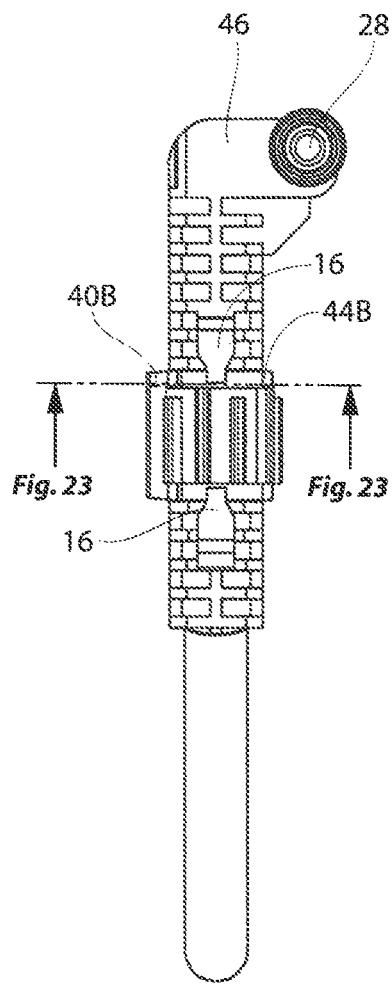
FIG. 22 is a front view of an embodiment of the present invention.
Figure 23:
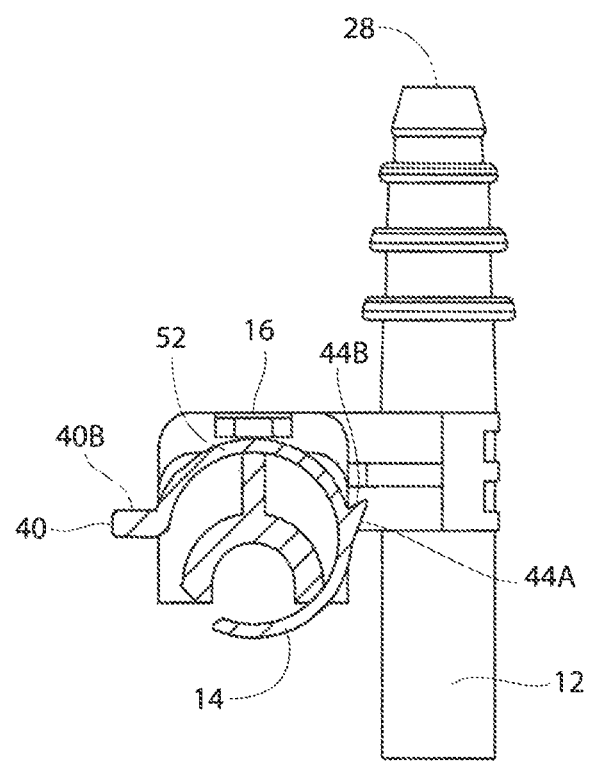
FIG. 23 is a cross sectional view of the embodiment of the invention taken from FIG. 22.

Turning now to FIGS. 10-12, locking ring 14 is rotatable from an open position (FIG. 11), in which stop rib 44 is positioned with its stop segment 44B against tabs 16. In a locked position (FIG. 12), ring end 40 is positioned with its ring end 40B against tabs 16. In this way, ring 14 can be finger or thumb rotated to an open position so that bougie 12 can be inserted or removed from handle 10, or can be rotated to a closed position to prevent bougie 12 from moving during intubation. FIGS. 22 and 23 further illustrate the relationship of the parts to one another.

Figure 3:
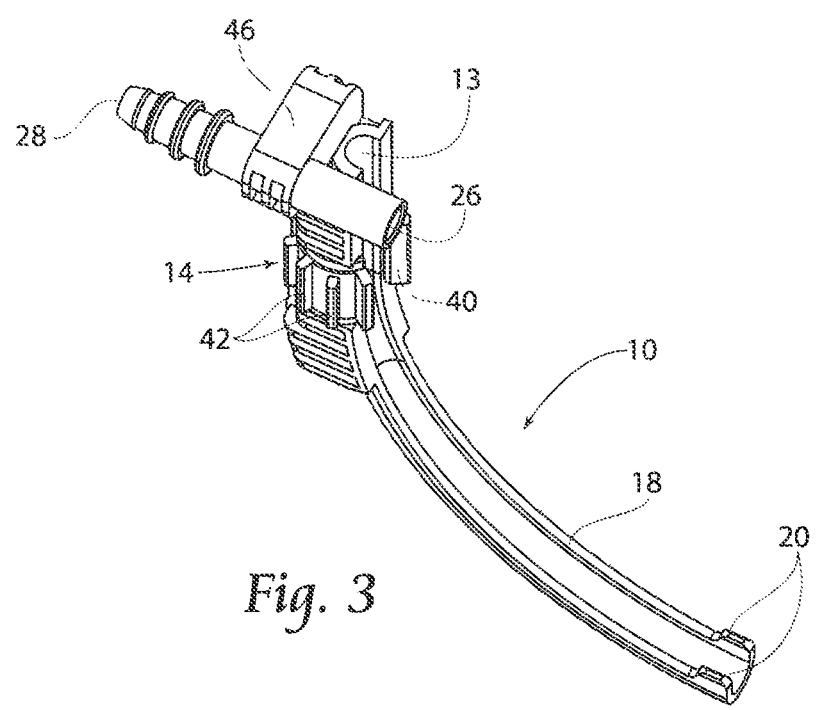
FIG. 3 is a rear perspective view of the device of FIG. 2.

Returning to FIGS. 2 and 3, handle 10 is shown without bougie 12. This permits groove 13 to be shown. It can be seen that channel 18 is curvilinear to create and support specific bending of the tube. In other words, bougie 12 will retain a curved shape using the curved channel 18 during a procedure where such curvature helps insert the bougie 12.

Figure 13:
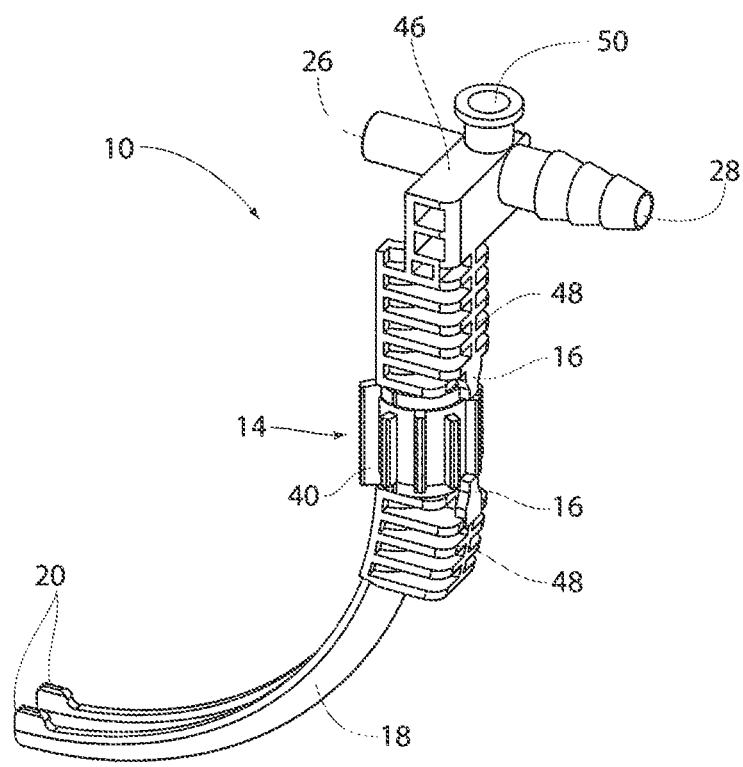
FIG. 13 is a perspective view of the gripping device according to the present invention, now showing a release valve.
Figure 14:
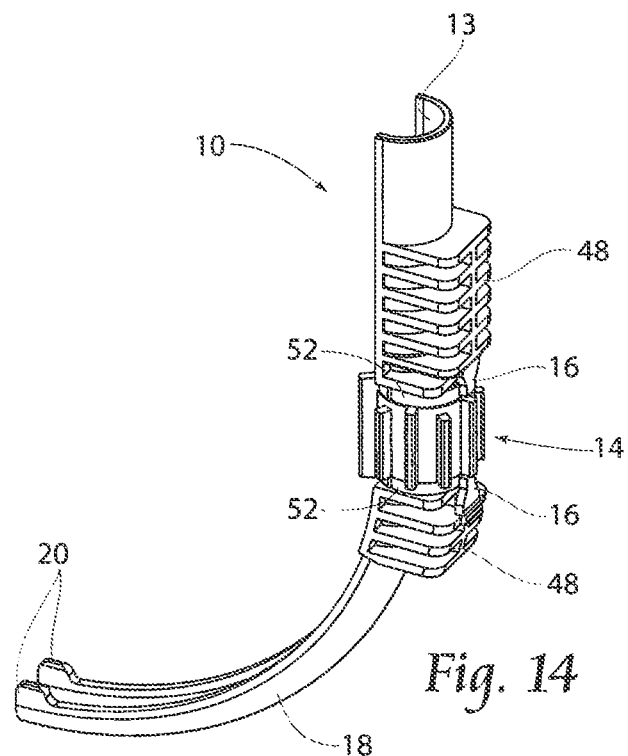
FIG. 14 is a front perspective view of the handle and ring.
Figure 15:
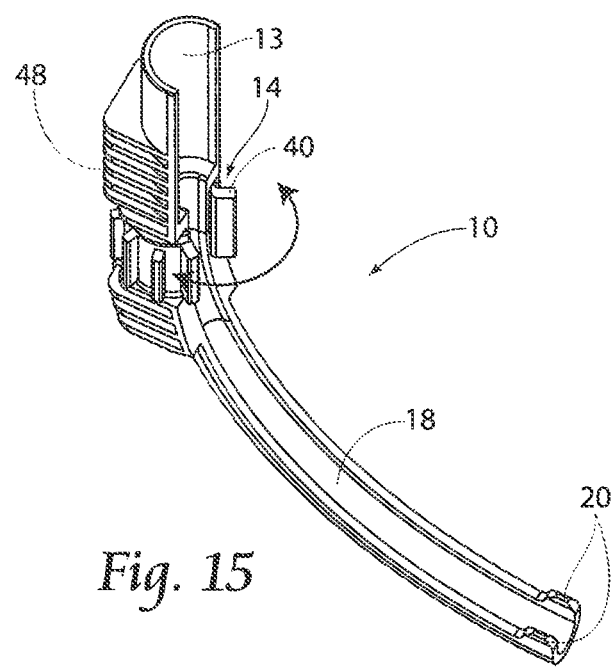
FIG. 15 is a rear perspective view of the handle and ring.

FIG. 13 shows an alternate embodiment in which a finger valve 50 is provided for manual venting. FIGS. 14 and 15 show handle 10, ring 14, tabs 16, support channel 18, channel retainers 20, leading finger member 40, gripping surfaces 48, and collars 52.

FIGS. 14 and 15 show an alternate embodiment in which elbow segment 46 is not provided. This embodiment is useful for placing a bougie when an inlet 26, outlet 28, or valve 50 are unnecessary.

Figure 16:
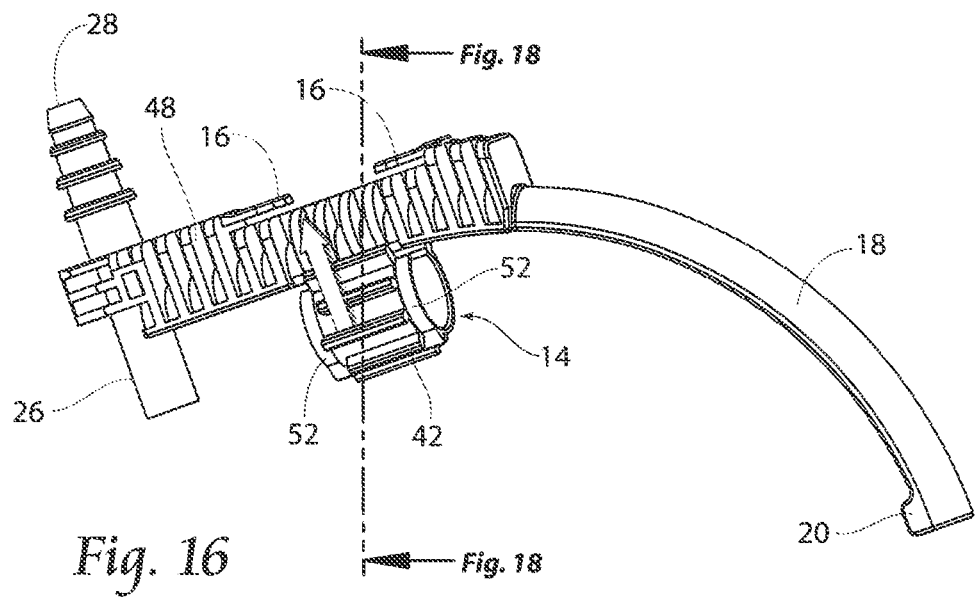
FIGS. 16-18 show the gripping handle from different angles while the ring is being installed.
Figures 17, 18:
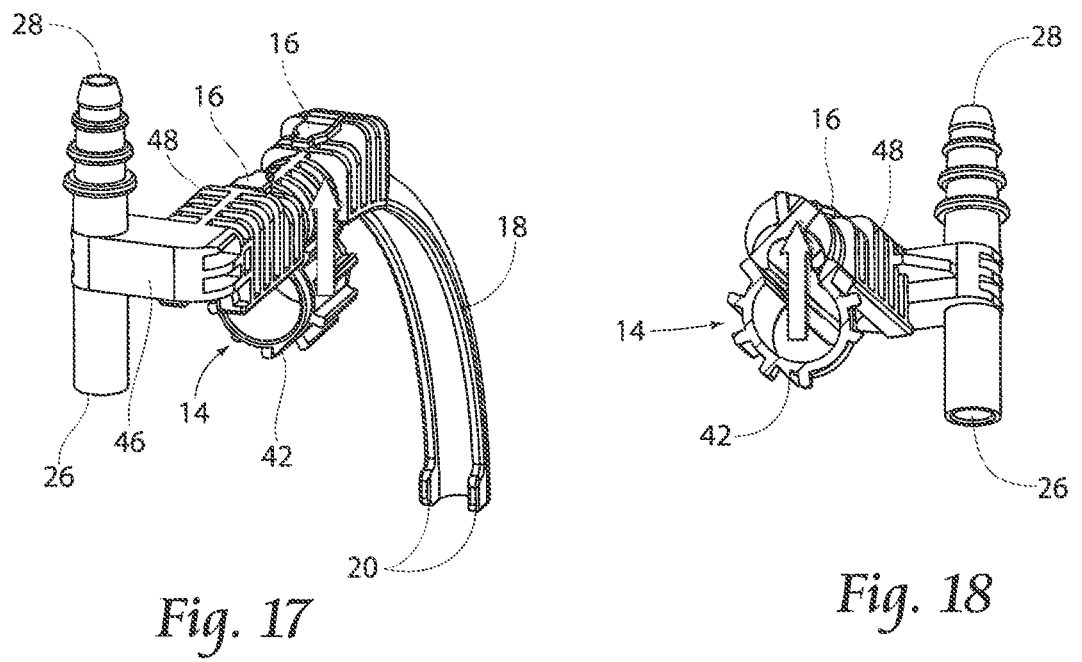

Turning now to FIGS. 16-18, installation of the ring onto the handle is initiated. Ring opening 36 is faced toward reduced diameter ring support section 34 and inserted until the leading finger member 40 is fastened adjacent to tabs 16 and surface 38 is in sliding contact with section 34.

Advantageously, as can be seen in FIG. 15, the user is capable of adjusting the locking ring 14 with a single hand, particularly the same hand that is holding the handle 10. The arrangement of the present invention and locking ring 14 allows for such improvements over the prior art, thereby providing more efficient intubation methods compared to the prior art. By locking the bougie 12 within channel 18, the user can reposition handle 10 and/or the bougie 12 without needing to separate handle 10 from bougie 12. Furthermore, the device allows the bougie 12 to slide within the device and the bougie 12 without fear of the bougie being inadvertently remove from the channel.

Figure 19:
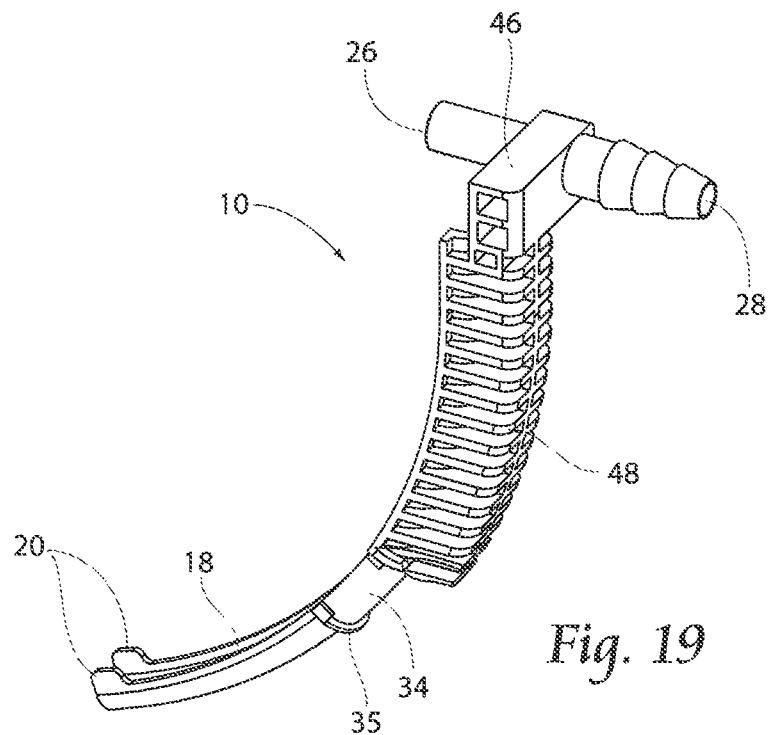
FIGS. 19-20 are alternate embodiments in which a ring is used below the handle rather than on the handle.
Figure 20:
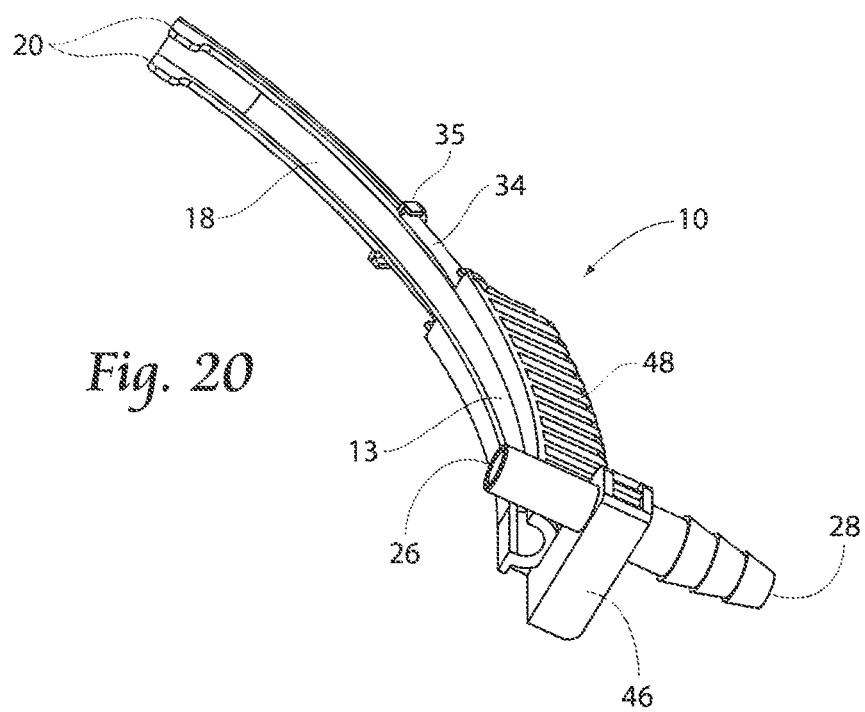

It is anticipated that reduced diameter section 34 will be placed generally centrally on handle 10 for easy finger/thumb control. However, FIGS. 19-20 show an embodiment of handle 10 in which gripping area 48 is provided separate from ring 14, i.e. below gripping area 48 at segment 34. In this embodiment, a retainer 35 is provided to hold locking ring 14 in place.

Figure 21:
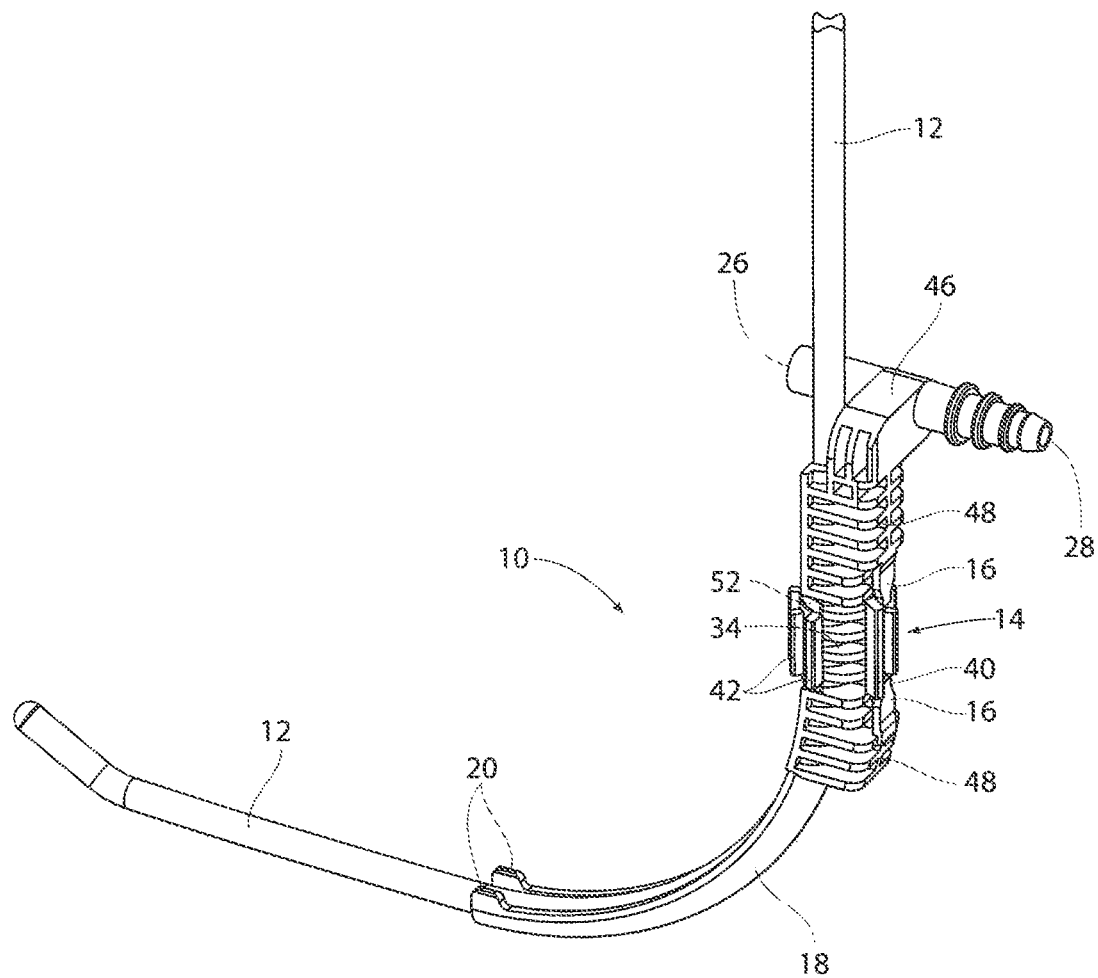
FIG. 21 shows another embodiment of the present invention.

FIG. 21 shows a bougie handle 10 and bougie 12. Bougie 12 is seated in groove 13 (not shown), extends through handle 10 to curved support channel 18, and is held in place with channel retainers 20 and locking ring 14. Locking ring 14 is shown in contact with tabs 16 over reduced diameter segment 34. Member 40 is shown adjacent to tabs 16, and at least one of collars 52 can be seen. Elbow segment 46 connects grasping segments 48 to inlet/outlet 26/28.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

I claim:

1. A device for gripping a bougie, the device comprising:
   a handle having a groove therein;
   a locking ring; and
   a longitudinally curved support channel extending from said groove;
   wherein said bougie is secured within said groove by way of said locking ring,
   at least one stop tab located on said handle;
   wherein said locking ring has at least one stop rib with at least one sloped surface and at least one stop surface, wherein said stop surface prevents movement of said ring past said stop tab and wherein said sloped surface permits movement of said ring under and past said stop tab.

2. The device of claim 1, wherein said locking ring is rotatable about said handle to secure said bougie within said groove.

3. The device of claim 1, wherein said handle has a reduced diameter portion and wherein said locking ring is sized to fit over said reduced diameter portion.

4. The device of claim 3, wherein said reduced diameter portion is located generally centrally on said handle.

5. The device of claim 3, wherein said at least one stop tab that interferes with the ability of said ring to rotate.

6. The device of claim 5, wherein said stop tab is flexible.

7. The device of claim 1, wherein said ring has two ends and bears at least one collar extension on one of said ends.

8. The device of claim 7, wherein said ring hears a collar extension on each of said two ends.

9. The device of claim 1, wherein said locking ring has an opening for permitting said ring to be mounted on said handle, wherein said opening is adjacent on each side to a finger member, wherein said finger members form a portion of a V-shape.

10. The device of claim 9, wherein said opening is smaller than the diameter of said handle.

11. A method of intubation comprising the steps of:
providing a device according to claim 1;
squeezing a bougie into said groove, said squeezing carried out with gripping force of a user's fingers;
locking said locking ring, thereby keeping said bougie in position within said groove;
gripping said bougie and said handle together as one unit during said intubation;
positioning die bougie during the intubation process within an airway;
providing at least one collar extension, wherein said collar extends and is rotatably retained by said stop tab; and
rotating said locking ring to release said bougie.

12. A device for gripping a bougie, the device comprising:
a handle having a top end, a bottom end, and inner surface forming aside opening and exterior surface,
at least one stop tab located on said handle;
a locking ring having at least one stop rib with at least one sloped surface and at least one stop surface, wherein said stop surface prevents movement of said ring past said stop tab and wherein said sloped surface permits movement of said ring under and past said stop tab,
wherein said exterior surface comprises a gipping area and said gripping area is located opposite said side opening.

13. The device of claim 12, wherein said gripping area comprises a plurality of ridges.

14. The device of claim 12, wherein said device has an inlet and outlet at said top end.

15. The device of claim 12, further comprising a support channel bearing tube retainers.

16. The device of claim 12, further comprising a channel having a channel groove therein, wherein said support channel extends from said groove, and wherein said support channel is longitudinally curved.

17. The device of claim 16, further comprising a finger valve on said handle.

18. The device of claim 16, wherein said bottom end of said handle has a reduced diameter section.

* * * * *

UNITED STATES PATENT AND TRADEMARK OFFICE
CERTIFICATE OF CORRECTION

| | | |
|---|---|---|
| PATENT NO. | : 11,724,053 B2 | Page 1 of 1 |
| APPLICATION NO. | : 16/837122 | |
| DATED | : August 15, 2023 | |
| INVENTOR(S) | : Boyi Gao | |

It is certified that error appears in the above-identified patent and that said Letters Patent is hereby corrected as shown below:

In the Claims

Claim 8 Line 1: Delete "hears" and insert -- bears --

Claim 12 Line 3: Delete "aside" and insert -- a side --

Signed and Sealed this
Fifteenth Day of July, 2025

Coke Morgan Stewart
*Acting Director of the United States Patent and Trademark Office*